(12) United States Patent
Piletsky et al.

(10) Patent No.: US 7,682,836 B2
(45) Date of Patent: Mar. 23, 2010

(54) SELECTIVE BINDING MATERIALS

(75) Inventors: Sergiy Anatoliyovich Piletsky, Cranfield (GB); Olena Volodimirivna Piletska, Cranfield (GB); Khalku Karim, Cambridge (GB); Anthony Peter Francis Turner, North Crawley (GB); Alessandra Bossi, Varese (IT)

(73) Assignee: Cranfield University, Bedfordshire (GB)

( * ) Notice: Subject to any disclaimer, the term of this patent is extended or adjusted under 35 U.S.C. 154(b) by 253 days.

(21) Appl. No.: 10/381,593

(22) PCT Filed: Oct. 4, 2001

(86) PCT No.: PCT/GB01/04446

§ 371 (c)(1),
(2), (4) Date: Sep. 11, 2003

(87) PCT Pub. No.: WO02/29412

PCT Pub. Date: Apr. 11, 2002

(65) Prior Publication Data

US 2004/0063112 A1    Apr. 1, 2004

(30) Foreign Application Priority Data

Oct. 4, 2000    (GB)    ................... 0024276.8

(51) Int. Cl.
*G01N 33/551*    (2006.01)
(52) U.S. Cl. ................ 436/524; 435/5; 435/6; 435/7.2; 435/7.32; 436/815; 436/816; 436/817; 436/818; 436/901
(58) Field of Classification Search ......... 435/174–182, 435/803, 40.52; 436/518–535, 161, 147, 436/151, 181; 422/68.1–70; 264/28, 219–227; 204/451, 462, 468, 549, 550, 551
See application file for complete search history.

(56) References Cited

U.S. PATENT DOCUMENTS

| 1,755,795 | A | * | 4/1930 | Rhodes | .................. 249/66.1 |
| 4,466,936 | A | * | 8/1984 | Schapel | .................. 264/225 |
| 5,756,717 | A | | 5/1998 | Paliwal et al. | |
| 5,858,296 | A | * | 1/1999 | Domb | .................. 264/330 |
| 6,051,372 | A | * | 4/2000 | Bayerl et al. | .................. 435/4 |
| 6,129,896 | A | * | 10/2000 | Noonan et al. | ........... 422/82.05 |
| 6,713,309 | B1 | * | 3/2004 | Anderson et al. | ........... 436/518 |

FOREIGN PATENT DOCUMENTS

EP    0 797 096    9/1997

OTHER PUBLICATIONS

Lin JM, et al. Temperature Effect on Chiral Recognition of Some Amino Acids with Molecularly Imprinted Polymer Filled Capillary Electrochromatography. Biomed. Chromatogr. 1997;11:298-302.*
Nicholls IA, et al. Recognition and enantioselection of drugs and biochemicals using molecularly imprinted polymer technology. Trends Biotechnol. 1995;13:47-51.*
Nicholls, I.A. et al. Recognition and enantioselection of drugs and biochemicals using molecularly imprinted polymer technology. Trends Biotechnol. 1995;13:47-51.*
Harris, Quantitative Chemical Analysis, 4d., W.H. Freeman & Co. (1995). pp. 713-728.*
P.K. Owens et al.: "Molecular imprinting for bio- and pharmaceutical analysis" TRAC, Trends in Analytical Chemistry, vol. 18, No. 3, pp. 146-154 Mar. 1999.

* cited by examiner

*Primary Examiner*—Christopher L Chin
(74) *Attorney, Agent, or Firm*—Oblon, Spivak, McClelland, Maier & Neustadt, L.L.P.

(57) ABSTRACT

A template (a molecule preferably of molecular size >500 Da, or a larger entity such as a cell, virus or tissue sample) is dissolved or suspended in a fluid. The fluid is frozen, and the template is removed (e.g. by dissolution or electrophoresis, or mechanically) to leave an "imprinted" frozen fluid. This is capable of selectively adsorbing the template substance. It is usable as a separation medium, a recognition element in sensors and assays, and as a catalyst.

9 Claims, 3 Drawing Sheets

SELECTIVE BINDING MATERIALS

TECHNICAL FIELD

The present invention relates to selective binding materials, their preparation and uses.

BACKGROUND ART

Polyakov in the 1930's described substrate-specific materials prepared by condensing silicic acid in the presence of template molecules (Zhur.Fiz.Khim.2:799 (1931); 10:100(1937); 4:454 (1933)). More recent workers have used organic monomers, polymerized in the presence of template molecules (e.g. U.S. Pat. Nos. 5,110,833, 5,728,296, 5756717, WO 9641173).

DISCLOSURE OF INVENTION

In a first aspect the present invention provides a process for preparing a selective binding material capable of selectively binding a template material comprising:
   (a) preparing a composition comprising template material and a carrier fluid;
   (b) freezing the composition; and
   (c) at least partially removing template material from the frozen composition so as to leave frozen carrier fluid with binding sites where template material has been removed.

The template material may be selected from proteins, biological receptors, nucleic acids, chromosomes, cells, viruses, microorganisms, tissue samples, carbohydrates, oligosaccharides, polysaccharides, nucleoproteins, mucoproteins, lipoproteins, synthetic proteins, glycoproteins, glucosaminoglycans, steroids, immunosuppressants, hormones, heparin, antibiotics, vitamins and drugs.

The carrier fluid may be selected from water, aqueous solvents, aqueous solutions, inorganic liquids, organic solvents, metals, fusible organic compounds, fusible inorganic compounds, polymers and gases. When the template material is molecular, the fluid will generally be a solvent therefor. The composition may be a suspension, as it generally will be if the template material is a complex entity, such as a tissue sample. Molten metals will generally be restricted to low melting metals e.g. mercury and gallium. Gases that can be liquefied and solidified by control of temperature and/or pressure may also be used.

Preferred compositions are aqueous solutions, e.g. of proteins.

A composition may be a 2-phase system, e.g. with the template material partitioned between immiscible solvents (e.g. water and an organic solvent such as chloroform or ether). Only the higher-freezing one of these may be frozen in step (b).

When the template material is soluble, step (c) will usually involve its dissolution, preferably using a solvent in which the frozen carrier fluid is not substantially soluble (e.g. using chloroform, acetonitrile or other organic solvents or mixtures to remove materials from ice). Suitable materials may be removed by electrodialysis. Particularly for particulate material, mechanical removal may be appropriate.

The invention preferably uses template molecules of molecular size exceeding 500 Da.

The frozen imprinted fluid has predetermined affinity and specificity superior to non-imprinted material and can be prepared much more easily than traditional cross-linked imprinted polymers. Materials prepared as described in this invention can be used as adsorbents in separation and purification, as catalysts and as recognition materials in sensors and assays.

In a second aspect the present invention provides a selective binding material as prepared by the above process.

In further aspects the invention provides uses of such materials exploiting their selective binding abilities. Use as a separation matrix is exemplified below. An example of use in a sensor or array could involve using our materials in place of antibodies in immunosensors and assays employing them. An example of use as a catalyst would involve employing a transition state analogue as the template material to produce a material capable of catalysing a reaction that proceeds through such a transition state.

In a yet further aspect the invention provides a process for preparing and using a selective binding material comprising:
   (a) preparing a composition comprising template material and a carrier fluid;
   (b) freezing the composition; and
   (c) contacting the frozen composition with a solution containing a molecular species which selectively interacts with template material in the frozen composition.

Traditional imprinting polymerisation includes formation of a rigid polymer network around a template which may be a small organic substance, such as a drug, or a protein or even a cell. Molecularly imprinted polymers (MIPs) prepared in this way consist of monomer units linked together by predominantly covalent interactions.

The present invention, in various aspects, describes the formation of the substrate-specific material by freezing the solvent or other fluid in the presence of a template. In contrast to traditional MIP preparation, where solvent plays a secondary role, being at most a reaction medium which facilitates the complex formation between the functional monomers and the template, this new approach relies on the ability of the frozen solvent to act as adsorbent. When prepared in the presence of template, frozen solvent contains cavities occupied by template molecules which can be emptied and used for rebinding of the template molecules. The structure of the imprints formed should be complementary to the structure of the template or molecules with structure and shape similar to those of the template molecules.

In embodiments in which template material is not removed from the frozen carrier fluid, template will remain immobilised. At least part of the molecules, suspension particles or tissue will remain exposed and available for a subsequent action (recognition, binding, catalysis, sensing etc.). Such material can be used as a separation matrix, element of sensor or assay and as a catalyst.

Figure 1:
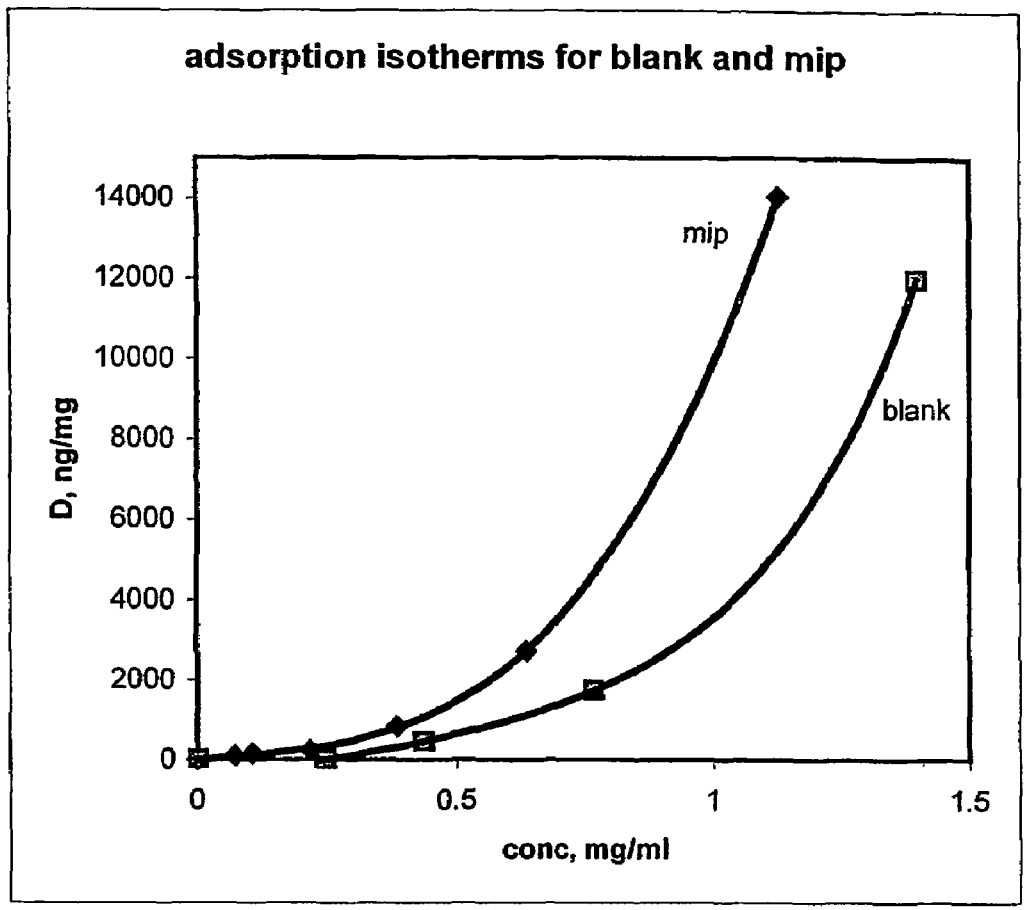
FIG. 1 shows adsorption isotherms comparing adsorption of a template material to ice formed in the presence of the material ("mip") and ice formed in its absence. The absorption isotherms in FIG 1 show the absorption of analyte in nanograms of analyte absorbed per milligram of mip or blank.

Sephadex G25, 30 mg/sample were transferred into the wells of filtration microplates and swelled overnight in 0.2 ml 1 mg/ml solution of(+)-isoproterenol (+)-bitartrate salt. The excess of solution was removed by filtration under reduced pressure and adsorbent was flushed twice with 0.2 ml chloroform. The swelled adsorbent was frozen for 12 hours at −15° C. Adsorbent was washed four times with acetonitrile at −15° C. Blank material was prepared in the same way but in the absence of isoproterenol. The adsorption properties of prepared adsorbents were evaluated by adding 0.15 ml aliquot of the corresponding analyte in the concentration ranging from 0.1 to 10 mg/ml. Concentration of isoproterenol in solution was measured spectrophotometrically at 280 nm. Results of the sorption analysis indicate that ice, prepared in the presence of template has higher affinity to the template than blank sample (FIG. 1). Sephadex G25 itself has no affinity to isoproterenol.

Figure 2A:
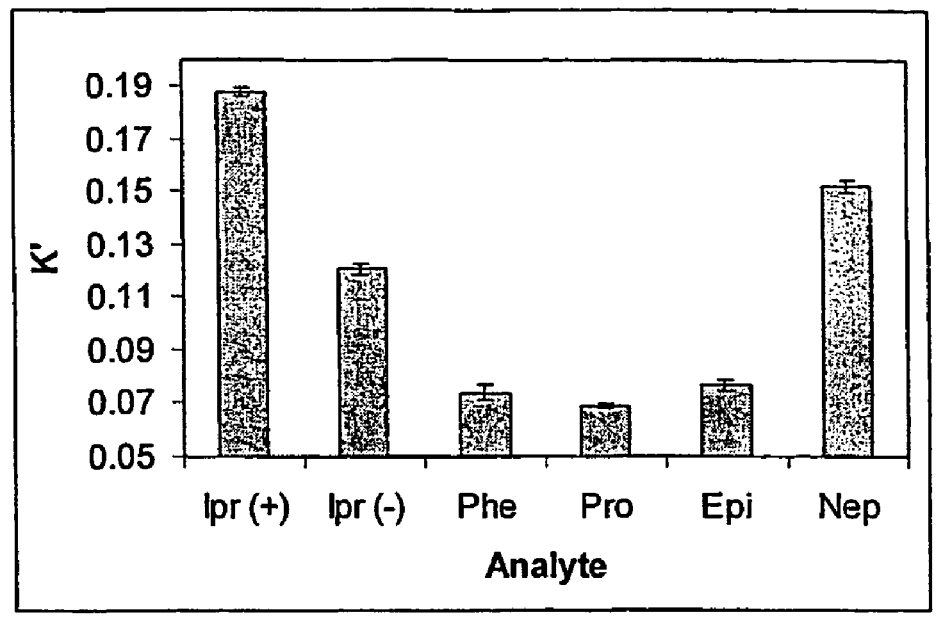
FIGS. 2(a) and 2(b) show capacity factors K' (a) and separation factors (b) of a range of analytes passed through a column containing a selective binding material prepared in the presence of one of them.
Figure 2B:
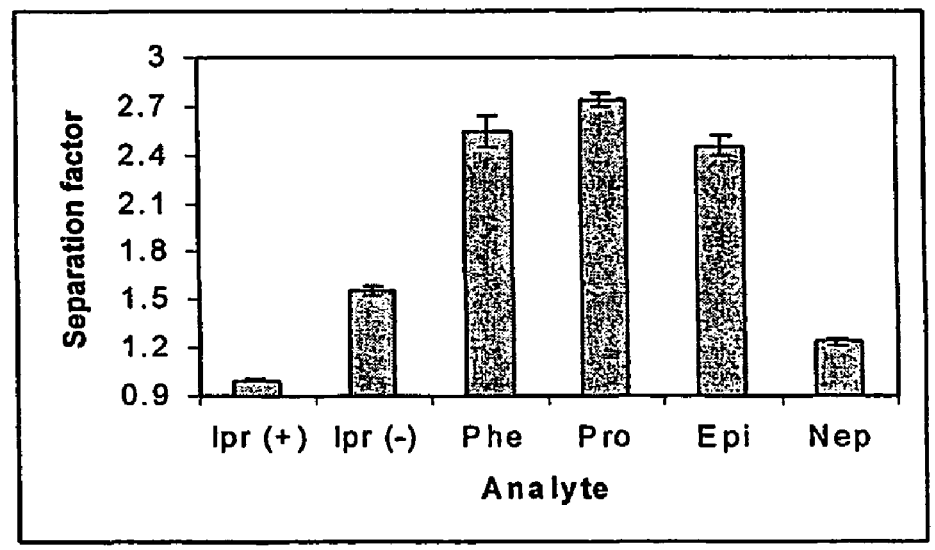

The same material, prepared in the presence of isoproterenol has been analysed by HPLC in experiments with compounds having structure similar to that of isoproterenol. Results of this analysis indicate that the ice has highest affinity to the target compound presented in solution (FIG. 2). An HPLC column (100×4.6 mm i.d.) was packed with approximately 1 g Sephadex G25 swelled in 1 mg/ml (+) isoproterenol (MIP) or water (Blank). Column was washed with chloroform and frozen at −15° C. for 12 hours. All chromatographic experiments were performed at −10° C. using detection at 280 nm and flow rate 1 ml/min. The column was washed on-line with acetonitrile until a stable baseline was obtained and solvent replaced with 10% aqueous acetonitrile. 20 μl solution of the analyte in 0.1 mg/ml concentration were used for the injections. Ipr (+)-(+) isoproterenol, Ipr (−)-(−) isoproterenol, Phe—phenylephrine, Pro—propranolol, Epi—epinephrine, Nep—norepinephrine.

Figure 3:
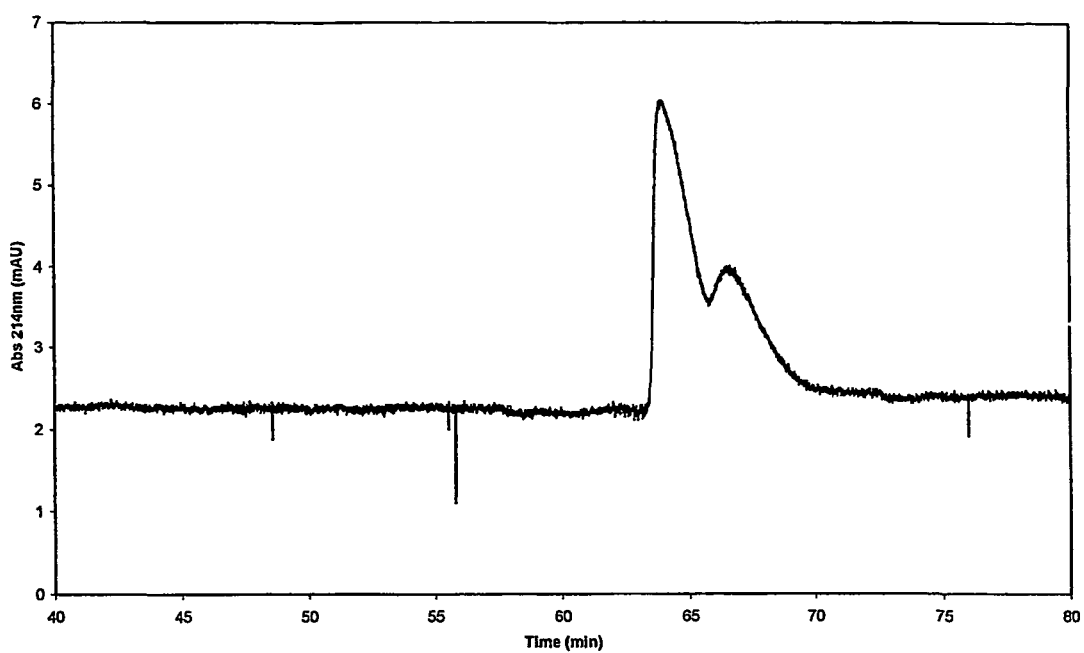
FIG. 3 is a trace showing the result of electrophoresis of a mixture of D- and L-phenylalanine in a capillary filled with ice, formed in the presence of L-phenylalanine.

The experiment was done using capillary electrophoresis unit Quanta 4000E, Waters. A 35 cm portion of capillary (fused silica, 80 cm, 100 um internal diameter—Polymicro Technologies, Hallow, UK) was inserted into insulated tubes connected with the refrigerating unit and cooled to a temperature of −14.5° C. The capillary was filled with a 2 mM solution of L-Phe in 9.5 mM HCl, and incubated at −14.5° C. for 1 hour, to allow complete refrigeration of the liquid inside the capillary lumen to form ice. To elute the L-Phe template from the ice a voltage of 13 kV was applied to the capillary and maintained until the baseline is stabilised. The sample, D-Phe, L-Phe or the racemate, diluted to a concentration of 2 mM in 9.5 mM HCl were injected hydrodinamically into the capillary for 6 sec. The run was performed by applying 13 kV (the current is 10 uA). The same experiment was performed using blank ice, formed in the absence of the template. The result of this analysis shown that the ice formed in the capillary in the presence of the L-Phe has enhanced affinity to the template and can be used to separate optical enantiomers (FIG. 3). No separation of L-Phe and D-Phe was observed when control (blank) ice filled capillary was used.

The invention claimed is:

1. A process for forming a selective binding material comprising:
   (a) preparing a composition by suspending or dissolving a template material into a carrier wherein said carrier is in a liquid state;
   (b) freezing the composition to convert said carrier from a liquid state to a solid state and forming a solid composition; and
   (c) at least partially removing the template material from the solid composition to leave solid carrier with binding sites at locations where the template material has been removed, to form a selective binding material, wherein the carrier is selected from the group consisting of water, aqueous solvents, inorganic liquids, organic solvents, metals, fusible inorganic compounds, and gases.

2. The process according to claim 1 wherein in step (c) the template material is removed mechanically.

3. The process according to claim 1 wherein in step (c) the template material is removed by washing with a solvent.

4. The process according to claim 1 wherein in step (c) the template material is removed by electrodialysis.

5. The process according to claim 1, wherein the template material is selected from the group consisting of proteins, biological receptors, nucleic acids, chromosomes, cells, viruses, microorganisms, tissue samples, carbohydrates, oligosaccharides, polysaccharides, nucleoproteins, mucoproteins, lipoproteins, synthetic proteins, glycoproteins, glucosaminoglycans, steroids, immunosuppressants, hormones, heparin, antibiotics, vitamins and drugs.

6. The process according to claim 1 wherein said carrier fluid is a liquid and said composition prepared in step (a) is a solution of the template material.

7. The process according to claim 6 wherein said carrier is water and the template material is a protein.

8. The process according to claim 1, wherein the template material is immobilised onto a solid support.

9. The process of claim 1, further comprising:
   (d) contacting the selective binding material with a solution comprising the template material to bind the template material at the binding sites of the selective binding material.

* * * * *